United States Patent [19]
Komine et al.

[11] Patent Number: 6,045,746
[45] Date of Patent: Apr. 4, 2000

[54] METHOD FOR PRODUCING RESIN ARTICLE HAVING UNDERCUT SHAPE

[75] Inventors: Shozo Komine, Chiba; Yoshiki Nishigaki; Hachiro Yamada, both of Osaka, all of Japan

[73] Assignee: Sumitomo Chemical Co., Ltd., Osaka, Japan

[21] Appl. No.: 08/972,571

[22] Filed: Nov. 18, 1997

[30] Foreign Application Priority Data

Nov. 18, 1996 [JP] Japan ................................. 8-306587

[51] Int. Cl.[7] .......................... B29C 49/06; B29C 51/34
[52] U.S. Cl. .................... 264/529; 264/532; 264/550; 425/529; 425/533
[58] Field of Search ................... 264/532, 529, 264/550, 531; 425/529, 533, 387.1

[56] References Cited

U.S. PATENT DOCUMENTS

| | | | |
|---|---|---|---|
| 3,244,778 | 4/1966 | Ninneman | 264/529 |
| 3,298,893 | 1/1967 | Allen | 264/532 |
| 3,892,830 | 7/1975 | Hudson et al. | 264/532 |
| 3,949,125 | 4/1976 | Roberts. | |
| 4,108,937 | 8/1978 | Martineu et al. | 264/529 |
| 4,465,199 | 8/1984 | Aoki. | |
| 5,403,538 | 4/1995 | Maeda | 264/532 |

FOREIGN PATENT DOCUMENTS

| | | |
|---|---|---|
| 0333400 | 9/1989 | European Pat. Off. . |
| 0427104 | 5/1991 | European Pat. Off. . |
| 669240 | 11/1929 | France . |
| 1278148 | 4/1962 | France . |
| 2508004 | 12/1982 | France . |
| 51-131567 | 11/1976 | Japan . |
| 55-49221 | 4/1980 | Japan . |
| 5-124095 | 5/1993 | Japan . |
| 2 294 467 | 5/1996 | United Kingdom . |
| 2294467 | 5/1996 | United Kingdom . |

*Primary Examiner*—Jan H. Silbaugh
*Assistant Examiner*—Dae Young Lee
*Attorney, Agent, or Firm*—Pillsbury Madison & Sutro LLP

[57] ABSTRACT

A resin molded article having a highly expanded undercut shape and a uniform wall thickness distribution is produced with good productivity by forming a parison as an intermediate molded article by injection molding a thermoplastic resin, expanding said parison in open molds prior to blow molding of the parison in the final shape, then closing the molds, and blow molding said parison in the closed molds to form the final shape of the article.

4 Claims, 4 Drawing Sheets

METHOD FOR PRODUCING RESIN ARTICLE HAVING UNDERCUT SHAPE

BACKGROUND OF THE INVENTION

1. Field of the Invention

Figure 5:
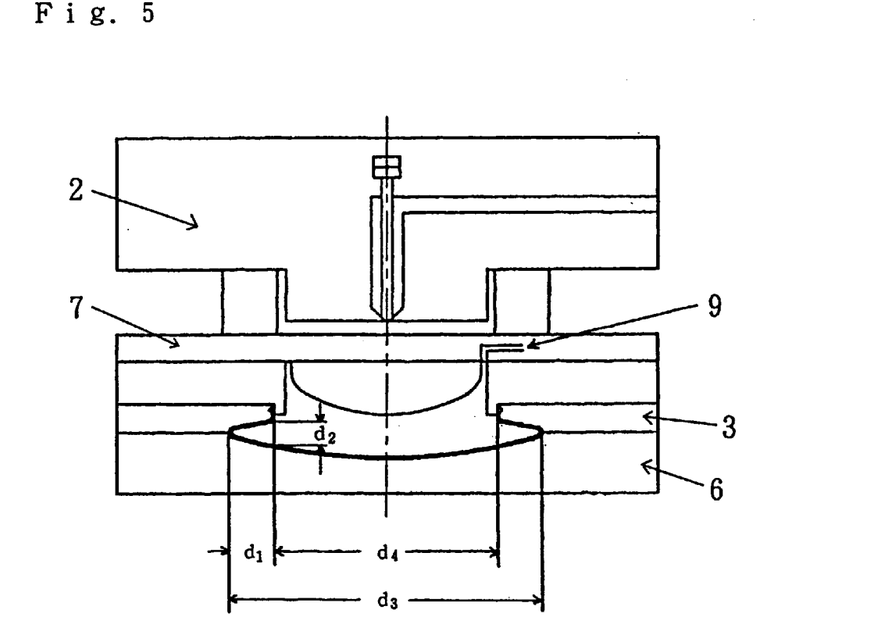
FIG. 5 shows the cross section of the molds in the step for blow molding the parison.

The present invention relates to a method for producing a resin article having an undercut shape, that is, a shape having a part which prevents removal of the molded article from a mold, by an injection blow molding method. Such a part is, for example, a part larger than an opening as shown in FIG. 5.

Resin articles having an undercut shape are used as shades of light fittings, containers, cases for industrial parts and parts of light electric appliances, and the like.

2. Description of the Related Art

In general, resin articles having an undercut shape are produced from thermoplastic resins by (1) injection molding, (2) press molding, (3) vacuum and pressure forming, and (4) injection blow molding. (1) The injection molding comprises the steps of providing male and female molds which leaves a space having the same shape as a resin article to be produced between them, supplying a synthetic resin in a molten state in the space, cooling and solidifying the resin, and then separating the molds to remove the resin molded article.

It is very difficult for the molds to have a structure from which the resin article is removed, when the outermost size of the resin article is larger than the opening of the article.

(2) The press molding comprises the steps of producing an intermediate resin article of a flat plate shape, placing the intermediate article which is still maintained at a high temperature on a female mold, and pressing the intermediate article between male and female molds to shape it in a desired shape.

However, it is impossible to press mold an article when its outermost size is larger than its opening. Furthermore, the press molding should be carried out using a line of large molding machines, since the intermediate article should be pressed while it is maintained at a high temperature.

(3) The vacuum or pressure forming comprises the steps of producing an intermediate resin article of a flat plate shape, placing the intermediate article on a female mold, clamping the periphery of the article, heating the clamped peripheral parts, and inflating the intermediate article to press it against the female mold by evacuating an air from the space between the female mold and intermediate article through an air vent hole provided in the female mold or by blowing a compressed air over the inner surface of the intermediate article.

In this molding method, shapes of projected parts are limited. Furthermore, articles which will be screwed in the opening cannot be produced because of the mold structure, and the clamped parts remaining at the periphery of the opening should be removed by post-processing. Furthermore, the molding cycle is prolonged and thus these methods are not suitable for mass production.

(4) The injection blow molding comprises the steps of producing an intermediate resin article having a shape similar to that of a final resin article by injection molding, removing a female mold while the intermediate article is maintained at a high temperature, inserting the intermediate article formed around a male mold in a female mold having the same shape as that of the final resin article, and inflating the intermediate article to press it against the female mold by blowing a compressed air through a hole provided in the male mold wall.

This method continuously carries out the injection molding and blow molding. Thus, the intermediate articles are less contaminated by handling such as transportation. The productivity of this method is high.

This method can produce a resin article having the outermost size which is larger than the opening to a certain extent, but the undercut shapes to be produced by this method are still limited.

The resin articles having the undercut shape which are produced by the above conventional methods have the increased tolerance of wall thickness as the outermost size becomes large in comparison with the opening. In particular, in the case of molded articles which have a small height and have been highly stretched such as shades of light fittings, tip ends of corners or corners of square shaped articles have thin walls, and thus the articles have the low strength for practical use. In addition, lamp images are seen through the thin wall parts in the case of light-diffusing type shades of light fittings.

Thus, all the conventional molding methods have the drawback that the undercut shapes to be produced are limited.

SUMMARY OF THE INVENTION

An object of the present invention is to provide a method for producing a resin molded article having an undercut shape, which can maintain a uniform wall thickness distribution and has good productivity, even when the article has the extremely stretched undercut shape.

Accordingly, the present invention provides a method for producing a resin molded article having an undercut shape comprising the steps of:

forming a parison as an intermediate molded article by injection molding a thermoplastic resin, expanding said parison in open molds prior to blow molding of the parison in the final shape, then closing the molds, and blow molding said parison in the closed molds to form the final shape of the article.

BRIEF DESCRIPTION OF THE INVENTION

FIGS. 1 to 6 illustrate the molds and production steps employed in the Examples for the production of resin molded articles according to the present invention.

FIGS. 7 and 8 illustrate the molds and production steps employed in the Comparative Examples for the production of resin molded articles by conventional injection blow molding.

DETAILED DESCRIPTION OF THE INVENTION

The thermoplastic resins used in the method of the present invention are those which can be injection molded. Examples of such thermoplastic resins are acrylic resins, polycarbonate, polystyrene, MS resins which are copolymers of methyl methacrylate and styrene, polypropylene, polyethylene, high density polyethylene, ABS resins, polysulfone resins, thermoplastic polyester resins, and the like.

The acrylic resins may be homopolymers of methyl methacrylate, while copolymers of methyl methacrylate -with a small amount of comonomers such as methyl acrylate, ethyl acrylate, butyl acrylate, 2-ethylhexyl acrylate, etc. are often used for the improvement of processability and heat stability.

Furthermore, a preferable example of the acrylic resin is a methyl methacrylate resin comprising 30 to 100 wt. % of a methyl methacrylate polymer with a branched structure which has a weight average molecular weight of between 80,000 and 400,000 and a molecular weight between branch points (expressed by a Z average molecular weight) of between 30,000 and 500,000 and 0 to 70 wt. % of a linear methacrylic resin, since it has good moldability and achieves the small wall thickness tolerance, that is, it can provide molded articles having a large undercut ratio (the ratio $d_1/d_2$ in FIG. 5).

The methyl methacrylate resins with the branched structure will be explained.

The methyl methacrylate resins with the branched structure are disclosed in GB 2294467, and copolymers of monofunctional monomers containing methyl methacrylate as a main component, and polyfunctional monomers copolymerizable with the monofunctional monomers.

The monofunctional monomers comprising methyl methacrylate mean methyl methacrylate itself, or mixtures of 50 wt. % or more, preferably 70 wt. % or more of methyl methacrylate and at least one other monofunctional monomer copolymerizable with methyl methacrylate.

When the amount of methyl methacrylate is less than 50 wt. %, the copolymers may not have good transparency and mechanical strength which are the characteristics of the methyl methacrylate polymers.

Examples of the copolymerizable monofunctional monomers are methacrylates (e.g. ethyl methacrylate, propyl methacrylate, butyl methacrylate, benzyl methacrylate, etc.), acrylates (e.g. methyl acrylate, ethyl acrylate, propyl acrylate, butyl acrylate, 2-ethylhexyl acrylate, etc.), unsaturated carboxylic acids (e.g. acrylic acid, methacrylic acid, maleic acid, itaconic acid, etc.), acid anhydrides (e.g. maleic anhydride, itaconic anhydride, etc.), esters having a hydroxyl group (e.g. 2-hydroxyethyl acrylate, 2-hydroxypropyl acrylate, monoglycerol acrylate, 2-hydroxyethyl methacrylate, hydroxypropyl methacrylate, monoglycerol methacrylate, etc.), amides (e.g. acrylamide, methacrylamide, diacetone acrylamide, etc.), nitriles (e.g. acrylonitrile, methacrylonitrile, etc.), nitrogen-containing monomers (e.g. dimethylaminoethyl methacrylate, etc.), epoxy group-containing monomers (e.g. allyl glycidyl ether, glycidyl acrylate, glycidyl methacrylate, etc.), styrene monomers (e.g. styrene, α-methylstyrene, etc.), and the like.

Examples of the copolymerizable polyfunctional monomers are ethylene glycol or its oligomers both terminal groups of which are esterified with acrylic or methacrylic acid (e.g. ethylene glycol di(meth)acrylate, diethylene glycol di(meth)acrylate, triethylene glycol di(meth)acrylate, tetramethylene glycol is di(meth)acrylate, etc.), dihydric alcohols hydroxyl groups of which are esterified with acrylic or methacrylic acid (e.g. neopentyl glycol di(meth)acrylate, hexanediol di(meth)acrylate, butanediol di(meth)acrylate, etc.), polyhydric alcohols (e.g. trimethylolpropane, petaerithritol, etc.) and their derivatives which are esterified with acrylic or methacrylic acid, aryl compounds having at least two alkenyl groups (e.g. divinylbenzene, etc.), and the like.

The weight average molecular weight (Mw) of the methacrylic polymers with the branched structure is usually between 80,000 and 400,000, preferably between 150,000 and 300,000, and the molecular weight between branch points expressed by a Z average molecular weight (Mzb) is between 30,000 and 500,000, preferably between 50,000 and 200,000.

When Mw is less than 80,000, the resins do not have sufficient mechanical strength or solvent resistance. When Mw exceeds 400,000, the resins have low melt flowability and thus the compositions comprising such resins have low moldability.

When the molecular weight between branch points (Mzb) exceeds 500,000, the tension of the resins during the melt stretching decreases, and thus the compositions comprising such resins have low moldability. When Mzb is less than 30,000, the resins have low mechanical strength, and the molded articles have unsatisfactory appearance.

Herein, Mw and Mz are measured by gel permeation chromatography (GPC) and a differential refractometer, respectively. The measuring methods for Mw and Mz are well known in the polymer field.

The molecular weight between branch points means an average of molecular weights between adjacent branch points of the polymers having the branched structure.

The molecular weight between branch points which is expressed by the Z average molecular weight is described in Polymer J., Vol. 3, No. 6, (1972) 729–738, the disclosure of which is hereby incorporated by reference, and calculated according to the following equations:

$$[(\pi_1)/(\pi_2)]^{10/6} = [(1+Bz/6)^{0.5} + 4Bz/3 \, \pi]^{-0.5} \quad (1)$$

$$Mzb = Mz/Bz \quad (2)$$

in which $\pi_1$ is an intrinsic viscosity at a point at which a molecular weight corresponds to Mz on a calibration curve showing the relationship of intrinsic viscosities against absolute molecular weights of polymers to be analyzed, which calibration curve has been obtained using a universal calibration curve representing the relationship of the products of the absolute molecular weights and intrinsic viscosities against the elution times in GPC for standard samples of linear methyl methacrylate polymers;

$\pi_2$ is an intrinsic viscosity at a point corresponding to the same Mz as that of the polymer to be analyzed on a calibration curve showing the relationship of the intrinsic viscosities against the absolute molecular weights of standard samples of linear methyl methacrylate polymers; and Bz is the number of branch points for the Z average molecular weight Mz.

The amount of the polymers having the molecular weight of 300,000 or more in the methyl methacrylate polymers having the branched structure is preferably between [14×(reduced viscosity)−6.8] wt. % and [14×(reduced viscosity)+11.2] wt. % when a reduced viscosity is 0.7 dl/g or less, or between [40×(reduced viscosity)−25] wt. % and [40×(reduced viscosity)−7] wt. % when a reduced viscosity is 0.7 dl/g or more.

A reduced viscosity used herein is measured at a polymer concentration of 1 g/dl in chloroform at 25° C.

When the amount of the methyl methacrylate polymers having the molecular weight of 300,000 or more is in the above range, the polymers have good balance between the flowability of the polymer and the tensile strength in a melt state. Therefore, the resin compositions also have good balance between the flowability and strength during melt stretching, and thus provide the good quality molded articles.

The crosslinking degree of the methyl methacrylate polymer having the branched structure is usually 3% or less, preferably 1% of less, more preferably about 0%, in terms of a gel content, that is, the weight percentage of insoluble potions in acetone based on the whole weight of the polymer.

The methyl methacrylate polymers having the branched structure may be prepared by polymerizing the above monofunctional monomers and components constituting polyfunctional units containing the above polyfunctional monomers optionally in the presence of chain transfer agents and/or polymerization initiators.

The components constituting the polyfunctional units includes the above polyfunctional monomers, polyfunctional chain transfer agents, and polyfunctional polymerization initiators. They may be used in admixture.

The amount of the components constituting the polyfunctional units is between 0.02 and 1 wt. % based on the weight of the monofunctional monomers.

The chain transfer agents may be those used in the polymerization of methyl methacrylate. The chain transfer agents include monofunctional chain transfer agents having one chain transferring functional group, and polyfunctional chain transfer agents having at least two chain transferring functional groups.

Examples of the monofunctional chain transfer agents are alkylmercaptans, esters of thioglycolic acid, and the like, and examples of the polyfunctional chain transfer agents are polyhydric alcohols (e.g. ethylene glycol, neopentyl glycol, trimethylolpropane, pentaerythritol, dipentaerythritol, tripentaerythritol, sorbitol, etc.) the hydroxyl groups of which are esterified with thioglycolic acid or 3-mercaptopropionic acid.

The amount of the chain transfer agent used in the polymerization for the preparation of the methyl methacrylate polymers having the branched structure is usually between $5 \times 10^{-5}$ mole and $5 \times 10^{-3}$ mole per one mole of the monofunctional monomers. The amount of the copolymerizable polyfunctional monomers is so selected that the number of the functional groups is between $1 \times 10^{-5}$ equivalent and [(moles of chain transfer agents)$-2.5 \times 10^{-4}$] equivalents per one mole of the monofunctional monomers.

The weight average molecular weight of the methyl methacrylate polymer having the branched structure can be controlled generally by the concentrations of the mainly used polyfunctional monomers, chain transfer agents and radical polymerization initiators.

The weight average molecular weight of the methyl methacrylate polymer having the branched structure is adjusted by suitably selecting the concentrations of the polyfunctional monomers and chain transfer agents in the above ranges by taking into consideration the fact that the weight average molecular weight increases as the concentration of the polyfunctional monomers increases, or the weight average molecular weight decreases, as the concentration of the chain transfer agents increases.

The molecular weight between the branch points can be adjusted by the concentration of the polyfunctional monomers. The molecular weight between the branch points decreases as the concentration of the polyfunctional monomers increases.

Alternatively, the molecular weight between the branch points decreases as the concentration of the polyfunctional chain transfer agents increases.

The amount of the polymers having the molecular weight of 300,000 or more increases as the concentration of the polyfunctional monomers increases.

The polymerization initiators include monofunctional polymerization initiators which generate one pair of radicals from one molecule, and polyfunctional ones which generate two or more pairs of radicals from one molecule.

Examples of the monofunctional polymerization initiators are azo compounds (e.g. 2,2'-azobis(2,4-dimethylvaleronitrile, azobisisobutyronitrile, dimethyl 2,2'-azobisisobutylate, etc.); organic peroxide compounds such as peroxyesters (e.g. tert.-butyl peroxypivalate, tert.-butyl peroxy-2-ethylhexanoate, cumyl peroxy-2-ethylhexanoate, etc.), and diacylperoxides (e.g. di(3,5,5-trimethyl)hexanoyl peroxide, dilauroyl peroxide, etc.); and the like.

Examples of the polyfunctional polymerization initiators include difunctional ones such as 1,1-bis(tert.-butylperoxy)-3,3,5-trimethylcyclohexane and di-tert.-butylperoxytrimethyl adipate; trifunctional ones such as tris-(tert.-butylperoxy)triazine; and tetrafunctional ones such as 2,2-bis(4,4-di-tert.-butylperoxycyclohexyl)propane.

In a case where the polymerization is terminated when a polymerization rate reaches 45 to 60 wt. % like bulk polymerization, the amount of terminal vinyl groups formed from the polyfunctional monomers can be decreased by the use of the tri- or higher polyfunctional polymerization initiators in comparison with the sole use of the polyfunctional monomers.

When the polyfunctional polymerization initiators are used, they may replace at least a part of the components constituting the polyfunctional units.

The polymerization initiators are used in a suitable amount for each polymerization method. The amount of the polymerization initiators is usually between 0.001 and 1 wt. parts, preferably between 0.01 and 0.7 wt. parts, per 100 wt. parts of the monomer or monomers.

The weight average molecular weight decreases as the amount of the polymerization initiators increases like in the case of the conventional methyl methacrylate polymers.

The linear methacrylic resins used in the present invention may be general-purpose methacrylic resins, and polymers of monofunctional monomers comprising methyl methacrylate as a main component.

The monofunctional monomers comprising methyl methacrylate as a main component include methyl methacrylate itself, and mixtures of 50 wt. % or more, preferably 70 wt. % or more of methyl methacrylate and the rest of at least one monofunctional monomer copolymerizable with methyl methacrylate.

The examples of the monofunctional monomers copolymerizable with methyl methacrylate are the same as those exemplified above.

The linear methacrylic resins have a weight average molecular weight Mw of between 70,000 and 200,000, preferably between 80,000 and 180,000.

When the weight average molecular weight is less than 70,000, the molded articles formed from the resin compositions have insufficient mechanical strength. When the weight average molecular weight exceeds 200,000, the polymers tend to have low melt flowability and thus low processability.

The methyl methacrylate polymers having the branched structure and linear methacrylic resins may be prepared by any polymerization method for the preparation of conventional methyl methacrylate resins, that is, suspension polymerization, bulk polymerization and emulsion polymerization.

The methyl methacrylate resin comprises 30 to 100 wt. % of the methyl methacrylate polymer having the branched structure and 0 to 70 wt. % of the linear methacrylic resin.

The methyl methacrylate resins may optionally contain various additives which are added to the conventional acrylic resins, for example, releasing agents, UV light absorbers, colorants, antioxidants, heat stabilizers, plasticizers, and the like.

The molding apparatuses used in the present invention may be conventional injection blow molding apparatuses having a mold clamping unit comprising an injection unit, a parison mold and a blow mold.

Now, the molding method according to the present invention will be explained by making reference to the accompanying drawings.

Figure 1:
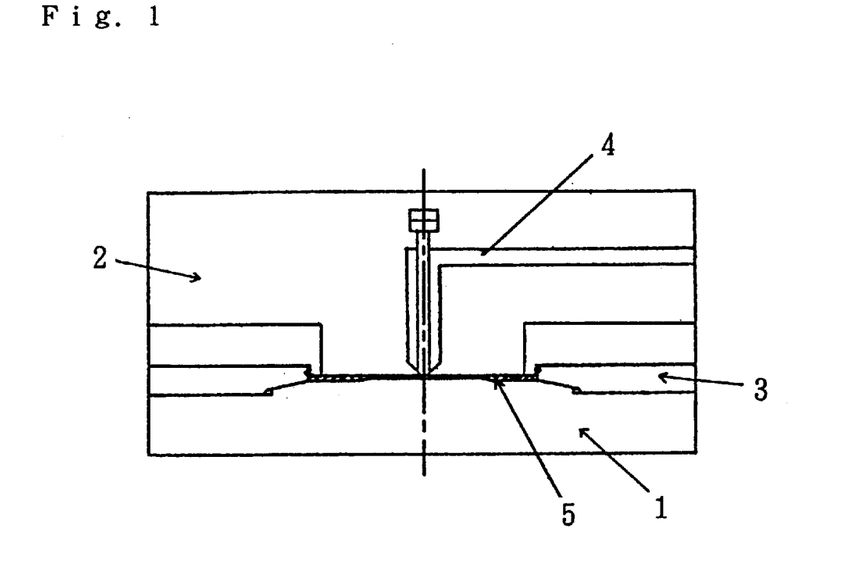
FIG. 1 shows the cross section of the molds in the step of the injection molding of the parison.

In an embodiment of the method of the present invention, as shown in FIG. 1, firstly a cavity mold 1 and a core mold 2 are closed. Then, a resin melt is injected from a hot runner 4 into a closed space surrounded by the molds 1, 2 and a neck mold 3, and a parison 5 is shaped as an intermediate resin molded article.

Figure 2:
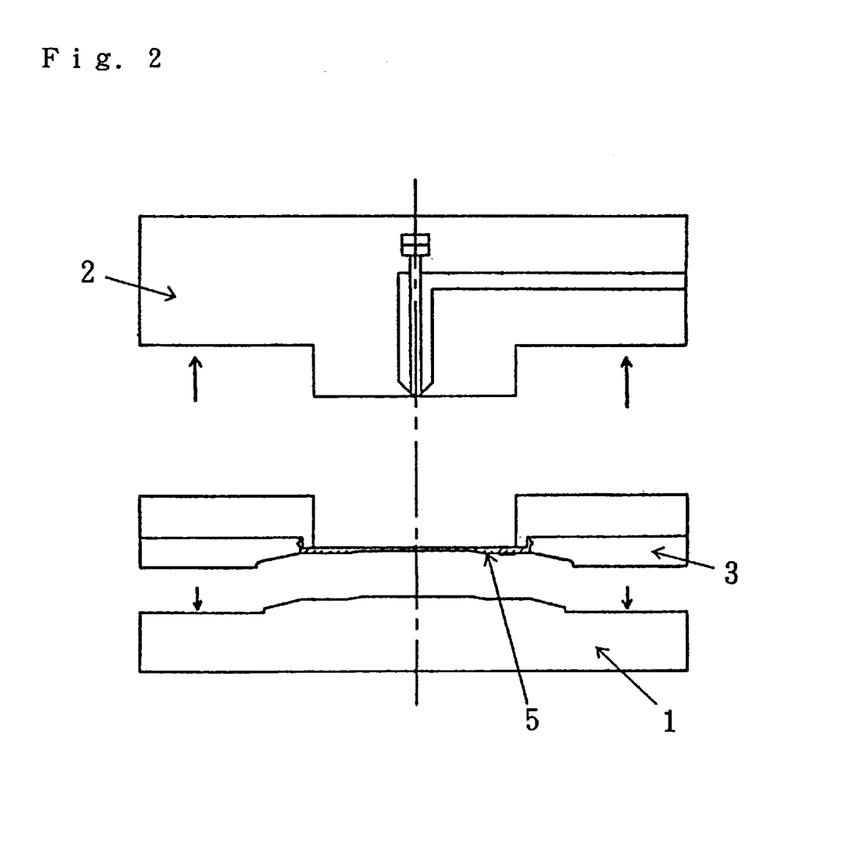
FIG. 2 shows the cross section of the molds in the open state after the molding of the parison.
Figure 3:
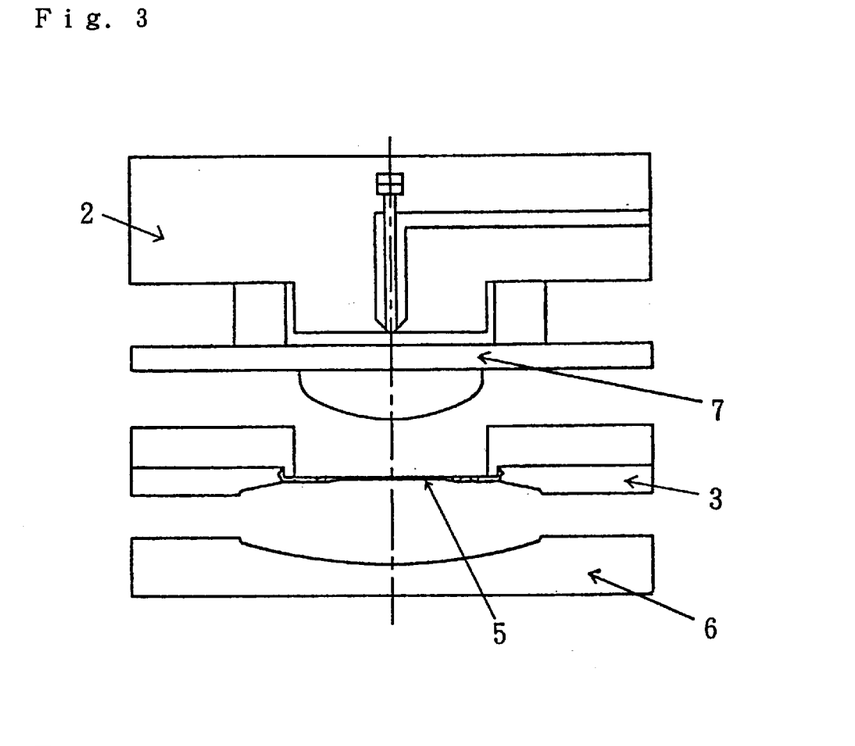
FIG. 3 shows the cross section of the molds during blow molding.

The cavity mold 1 and core mold 2 are opened as shown in FIG. 2, and then the neck mold 3 holding the parison 5 is moved into a space between a blow mold 6 and a plug mold 7, or the blow mold 6 and plug mold 7 are moved above and below the fixed neck mold 3, respectively as shown in FIG. 3. After that, the plug mold 7 and the neck mold 3 clamping the parison are closed while the blow mold 6 is in the open state.

Figure 4:
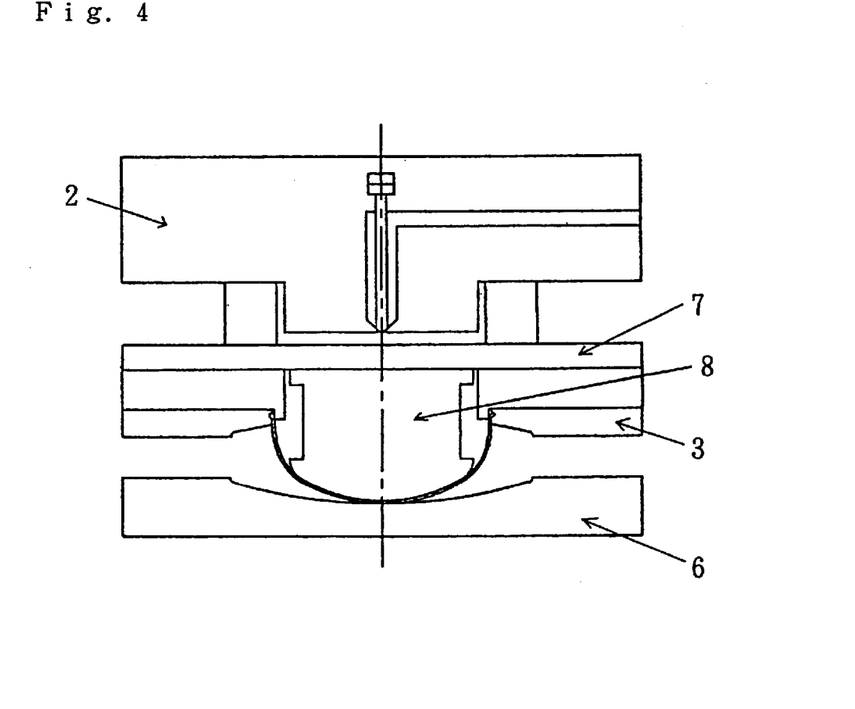
FIG. 4 shows the cross section of the molds in the step for expanding the parison prior to blow molding.

Next, as shown in FIG. 4, a plug 8 provided in the plug mold 7 is projected and extended so that the extended depth (height) becomes about 0.5 to 1.5 times the opening size.

Figure 6:
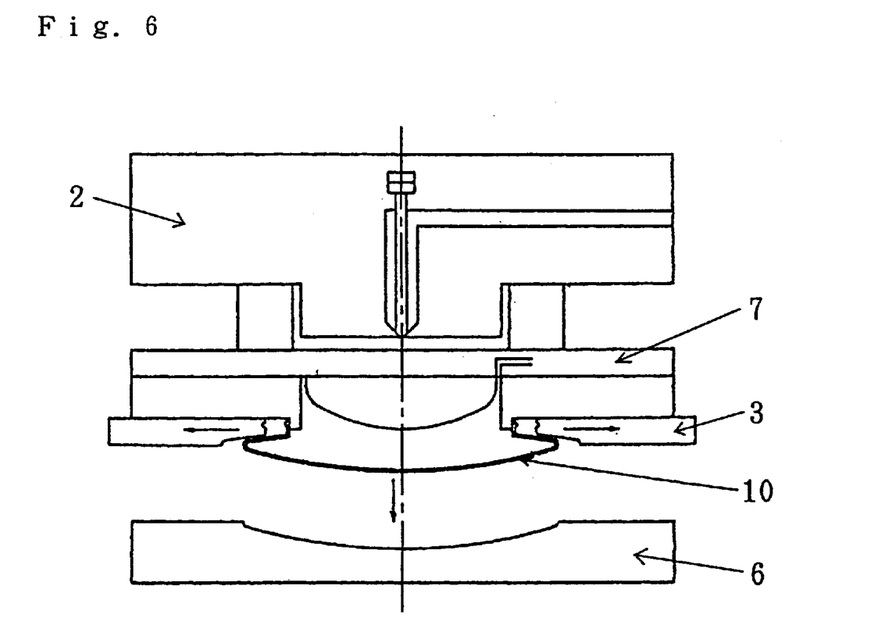
FIG. 6 shows the cross section of the molds in the open state after blow molding.

Then, as shown in FIG. 5, the plug 8 is retracted to the original position, and an air is blown through an air inlet 9 as soon as the blow mold 6 is closed. Thus, the resin is shaped in accordance with the shape of the blow mold 6. After cooling, the blow mold 6 and neck mold 3 are opened, and the resin molded article 10 is removed as shown in FIG. 6.

Figure 7:
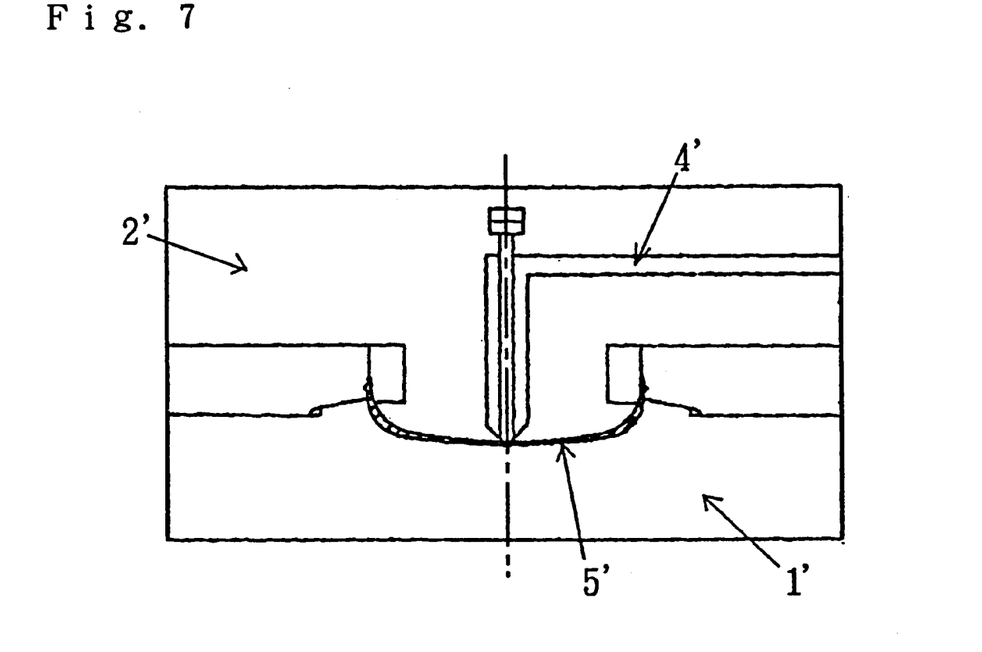
FIG. 7 shows the cross section of the molds in the step of the injection molding of the parison in the Comparative Examples.
Figure 8:
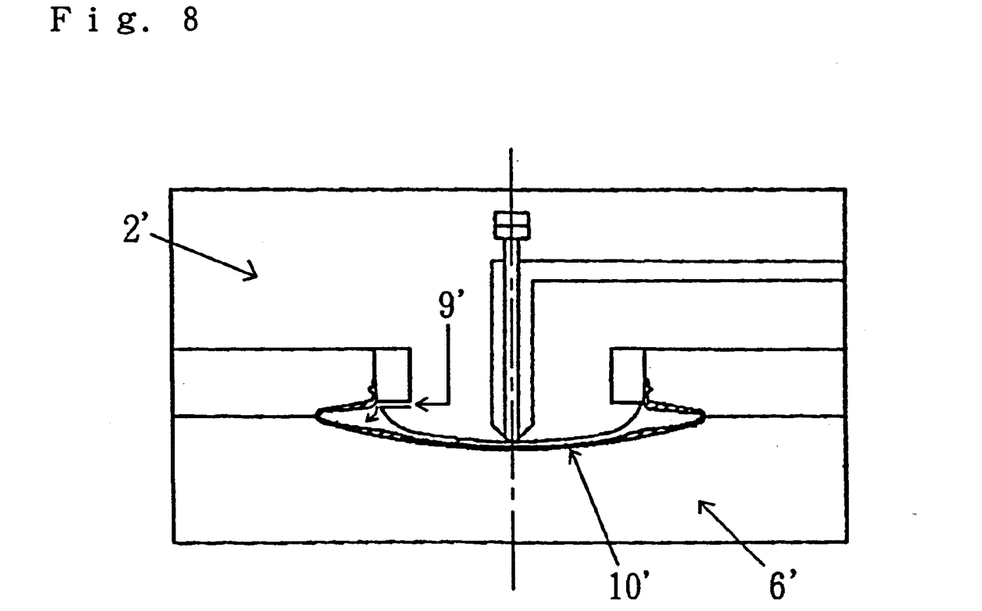
FIG. 8 shows the cross section of the molds in the step for blow molding the parison.

In the conventional injection blow molding method, as shown in FIG. 7, a resin melt is injected into a closed space between a cavity mold 1' and a core mold 2' through a hot runner 4', and a parison 5' having a semispherical shape in this case is formed as an intermediate resin molded article. Then, the core mold 2' holding the parison 5' is transferred onto a blow mold 6', and an air is injected in the blow mold 6' as soon as the core mold 2' and blow mold 6' are closed as shown in FIG. 8. Thus, the resin is shaped in accordance with the shape of the blow mold 6'. After cooling, the core mold 2' and blow mold 6' are opened and a resin molded article 10' is removed.

The blow molding step sometimes requires a longer time than the injection molding step of the parison depending on the wall thickness and/or shape of the article, and therefore the whole production efficiency of the process tends to deteriorate. In such a case, the molding step of the parisons and the blow molding step including the preliminary expansion of the parison are separated.

That is, the parisons are mass produced by the conventional injection molding method. Then, they are held by the neck molds, reheated and blow molded in the separate step.

This process can increase the productivity of the molding method, and also decrease the plant investment and the costs for the molds used in the blow molding step (molds for undercut shaping) greatly.

The injection molding temperature in the step for producing the parison is in the range between 170° C. and 300° C. Good parisons can be produced from general purpose acrylic resins in the temperature range between 190° C. and 260° C.

The parison is expanded prior to the blow molding to an extent that the expanded depth (height) is about 0.5 to 1.5 times the opening size.

Therefore, the opening degree of the molds during the expansion is determined by taking this height into account.

The expansion of the parison is carried out by a plug method comprising projecting a plug, a blow method comprising injecting a compressed air, or a combination of these methods.

The mold temperature in the expansion step and the conditions in the blow molding step for shaping the final product are suitably set according to the kinds of the resins, shapes of the molded articles, and the like.

The method of the present invention is effective for the production of deep draw articles having a molding area expansion ratio exceeding 100%, and molded articles having an undercut ratio of between 1.0 and 2.0 and an outermost size ratio of between 1.2 and 2.0.

Herein, the molding area expansion ratio is expressed by the following equation (3):

Molding area expansion ratio (%)=[(Average wall thickness of parison/average wall thickness of final molded article)−1 ]×100  (3)

The undercut ratio is expressed by the following equation (4):

Undercut ratio=[Length of undercut part ($d_1$)/maximum height of undercut part ($d_2$)]  (4)

The outermost size ratio is expressed by the following equation (5):

Outermost size ratio=[Outermost size ($d_3$)/opening size ($d_4$)]  (5)

The lengths of $d_1$, $d_2$, $d_3$ and $d_4$ are illustrated in FIG. 5.

When the parison is expanded with the compressed air or blowing against the already integrated blowing mold in the conventional methods for the production of the resin molded articles having the undercut shape, a part which is in contact with the inner wall of the mold is cooled and the expansion of that part is suppressed. Thus, the projected part (outermost peripheral part) has a very thin wall, or the parison is not expanded to the outermost size, and therefore the desired undercut shape is not obtained.

In the conventional injection blow molding methods, the uniformity of the wall thickness is achieved by the adjustment of the shape of the parison. However, the uniformity of the wall thickness is not sufficient with the article shape having the low height and large undercut.

According to the present invention, the contact of the parison to the inner wall of the blowing mold prior to the shaping of the projected part is prevented since the molds are once opened, and the parison is expanded. Thus, the uniformity of the wall thickness of the molded article can be much improved.

When the injection molding, preliminary expansion and blow molding are continuously carried out, the molded articles are produced at high productivity without the contamination from outside sources.

Furthermore, as already described, the productivity and reduction of production cost are much enhanced when the injection molding step of the parisons and the expansion and blow molding step are separately carried out.

The method of the present invention can produce the resin molded articles which have the large undercut, extremely uniform wall thickness distribution, and improved appearance and strength at high productivity while avoiding the contamination from outside.

When the resin molded articles produced by the method of the present invention are used as shades of light fittings, they have good uniformity at their peripheries, prevent lamp images from being seen through the shades, and provide uniform luminance distribution.

EXAMPLES

The present invention will be explained by the following examples, which will not limit the scope of the invention in any way.

In the examples, the properties were measured as follows:

(1) Wall thickness tolerance

A wall thickness distribution was measured in areas of a molded article except an opening (a neck part of a molded article).

(2) Tolerance ratio

A tolerance ratio was expressed by a ratio of the maximum wall thickness tolerance to the minimum one.

The large tolerance ratio means the low uniformity of the wall thickness of the molded article. A tolerance ratio exceeding 3 indicates that the uniformity of the wall thickness is not good.

(3) Undercut ratio of a molded article

An undercut ratio was calculated according to the equation (4) described above.

The molding is judged to be inadequate as this ratio becomes smaller than the undercut ratio of a mold.

(4) Appearance

The appearance of an opal-colored molded article was observed with an eye and ranked according to the following criteria:

A: Good

B: Fair although the color had irregularity partly.

C: The color was faded at the corners, and the transparent parts were conspicuous.

Example 1

A resin molded article was produced using the mold by the method explained in FIGS. 1 to 6.

A linear methacrylic resin was prepared according to Comparative Example 3 of BP 2294467 from 89.5 wt. parts of methyl methacrylate and 10.5 wt. parts of methyl acrylate, and heated and molten at 230 to 250° C. (MFR: 10.5 g/10 min.). Then, it was injection molded using a parison mold consisting of a core mold 2, a neck mold 3 and a cavity mold 1 and having a hot runner 4 as shown in FIG. 1, and a disc-form parison having a diameter of 255 mm and an average thickness of 2.5 mm was obtained as an intermediate resin molded article. The temperature of the parison mold was adjusted between 120 and 140° C.

Then, the core mold 2 and cavity mold 1 were opened as shown in FIG. 2, and a plug mold 7 and a blow mold 6 were shifted over and below the neck mold 3, respectively as shown in FIG. 3. The plug mold 7 was closed while maintaining the blow mold 6 in the open state, and the parison 5 was expanded with a plug 8 which was heated at 80 to 140° C. as shown in FIG. 4.

After that, the blow mold which was heated at 60 to 80° C. was closed while retracting the plug, and an air of 20 to 40° C. was blown in the blow mold under a pressure of 8 to 9 kgf/cm$^2$. Thus, the parison was molded in the final molded shape as shown in FIG. 5, which had an opening size of 250 mm, an outermost size of 350 mm, an average wall thickness of 1.0 mm, and an undercut ratio of 1.25.

After cooling, the blow mold 6 and neck mold 3 were disassembled, and the resin molded article 10 was obtained as shown in FIG. 6.

The parison shape, mold sizes, and parison temperature during expansion are listed in Table 1, and the moldability, article shape and appearance of the resin molded article are listed in Table 2.

As seen from Table 2, the obtained resin molded article had the uniform wall thickness distribution, the undercut shape which followed the shape of the blow mold, and good appearance.

Example 2

A resin molded article was produced in the same manner as in Example 1 except that the diameter of the parison mold was changed to 525 mm, the opening size and outermost size of the molded article was changed to 520 mm and 650 mm, and thus the undercut ratio increased.

As seen from Table 2, the obtained resin molded article had the uniform wall thickness distribution, the undercut shape which followed the shape of the blow mold, and good appearance.

Example 3

A resin molded article was produced in the same manner as in Example 2 except that a methyl methacrylate polymer having a branched structure was used, which had been prepared from 89.5 wt. parts of methyl methacrylate and 10.5 wt. parts of methyl acrylate in accordance with Example 2 of GB 2294467. This polymer had a weight average molecular weight of 160,000 and a molecular weight between branch points (expressed by a Z average molecular weight) of 130,000.

As seen from Table 2, the obtained resin molded article had the uniform wall thickness distribution, the undercut shape which followed the shape of the blow mold, and good appearance.

Example 4

A resin molded article was produced in the same manner as in Example 2 except that a polycarbonate resin (CALIBAR 2061–22M (opal colored) manufactured by SUMITOMO DOW Ltd.) was used as a resin, the injection molding temperature was between 250 and 320° C., the parison mold temperature was between 150 and 190° C., the blow mold temperature was between 80 and 120° C., and the plug mold temperature was between 80 and 160° C.

As seen from Table 2, the obtained resin molded article had the uniform wall thickness distribution, the undercut shape which followed the shape of the blow mold, and good appearance.

Comparative Example 1

A resin molded article was produced using the mold by the method explained in FIGS. 7 and 8.

A resin molded article was produced in the same manner as in Example 1 except that a semispherical parison having an average wall thickness of 3.5 mm) was formed by injection molding as shown in FIG. 7, a core mold 2' and a cavity mold 1' were opened, and a blow mold 6' was shifted below the core mold 2', and then the parison was blow molded without previous expansion, as shown in FIG. 8.

The properties of the obtained resin molded article are shown in Table 2. The molding was possible, but the molded article had poor appearance such that the center part and thin peripheral parts of the article had noticeable color shading.

Comparative Example 2

A resin molded article was produced in the same manner as in Example 2 except that a semispherical parison having an average wall thickness of 3.5 mm) was formed by injection molding as shown in FIG. 7, a core mold 2' and a cavity mold 1' were opened, and a blow mold 6' was shifted below the core mold 2', and then the parison was blow molded without previous expansion, as shown in FIG. 8.

The properties of the obtained resin molded article are shown in Table 2. The molding was possible, but the periphery of the molded article was very thin, and the article was partly broken.

Comparative Example 3

A resin molded article was produced in the same manner as in Comparative Example 2 except that the same resin as used in Example 3 was used.

The properties of the obtained resin molded article are shown in Table 2. The molding procedures were possible, but the molded article had poor appearance such that the center part and thin peripheral parts of the article had noticeable color shading.

The properties of the obtained resin molded article are

Comparative Example 4

A resin molded article was produced in the same manner as in Comparative Example 2 except that the same resin as used in Example 4 was used.shown in Table 2. The molding procedures were possible, but the molded article had poor appearance such that the center part and thin peripheral parts of the article had noticeable color shading.

TABLE 1

|  |  | Resin | Parison shape | Av. wall thickness of parison | Undercut ratio | Mold sizes Molding area expansion ratio (%) | Outermost size ratio | Parison temp. during expansion (° C.) |
| --- | --- | --- | --- | --- | --- | --- | --- | --- |
| Example | 1 | PMMA | D-shape | 2.5 | 1.25 | 170 | 1.40 | 170 |
|  | 2 | PMMA | D-shape | 2.5 | 1.63 | 195 | 1.25 | 170 |
|  | 3 | PMMA* | D-shape | 2.5 | 1.63 | 195 | 1.25 | 170 |
|  | 4 | PC | D-shape | 2.5 | 1.63 | 195 | 1.25 | 190 |
| Comp. Example | 1 | PMMA | Semisphere | 3.5 | 1.25 | 170 | 1.40 | 170 |
|  | 2 | PMMA | Semisphere | 3.5 | 1.63 | 195 | 1.25 | 170 |
|  | 3 | PMMA* | Semisphere | 3.5 | 1.63 | 195 | 1.25 | 170 |
|  | 4 | PC | Semisphere | 3.5 | 1.63 | 195 | 1.25 | 190 |

Notes:
PMMA: Polymethyl methacrylate.
PMMA*: PMMA having a branched structure.
PC: Polycarbonate.

TABLE 2

|  |  | Shape of molded article | | | | | |
| --- | --- | --- | --- | --- | --- | --- | --- |
|  |  | Blow moldability | Wall thickness tolerance | | | Undercut ratio | Appearance |
|  |  |  | Minimum (mm) | Maximum (mm) | Tolerance ratio |  |  |
| Example | 1 | Fair | 0.8 | 1.0 | 1.25 | 1.25 | A |
|  | 2 | Fair | 0.6 | 1.2 | 2.00 | 1.63 | A |
|  | 3 | Good | 0.8 | 1.1 | 1.38 | 1.63 | A |
|  | 4 | Fair | 0.7 | 1.1 | 1.57 | 1.63 | A |
| Comp. Example | 1 | Poor | 0.5 | 2.0 | 4.00 | 1.14 | C |
|  | 2 | Bad* | 0.3 | 2.2 | 7.30 | 1.22 | C |
|  | 3 | Poor–fair | 0.6 | 1.9 | 3.17 | 1.41 | B |
|  | 4 | Poor | 0.3 | 2.1 | 7.00 | 1.45 | C |

Note"
Bad*: Partly broken.

What is claimed is:

1. A method for producing a resin molded article having an undercut shape which has an undercut ratio of between 1.0 and 2.0, an outermost size that is 1.2 to 2.0 times an opening size, and a tolerance ratio of no greater than 3 comprising the steps of:

forming a parison as an intermediate molded article by injection molding a methyl methacrylate resin comprising at least 30 weight percent of a methyl methacrylate polymer with a branched structure which has a weight average molecular weight of between 80,000 and 400,000 and a molecular weight between branch points, as expressed by a Z average molecular weight, of between 30,000 and 500,000, expanding said parison in open molds prior to blow molding of the parison in the final shape, then closing the molds, and blow molding said parison in the closed molds to form the final shape of the article.

2. A method according to claim 1, wherein said parison is expanded by a plug method, a blow method or a combination of the plug and blow methods.

3. A method according to claim 1, wherein a depth of the expanded parison prior to blow molding is 0.5 to 1.5 times an opening size.

4. A method according to claim 1, wherein the resin molded article is a shade of a light fitting.

* * * * *